(12) United States Patent
Chen et al.

(10) Patent No.: US 10,846,855 B2
(45) Date of Patent: Nov. 24, 2020

(54) METHOD FOR CONVERTING SCAN INFORMATION OF A COMPUTED TOMOGRAPHY SCANNER INTO BONE PARAMETERS

(71) Applicants: HIWIN TECHNOLOGIES CORP., Taichung (TW); CHINA MEDICAL UNIVERSITY, Taichung (CN)

(72) Inventors: Yi-Wen Chen, Taichung (TW); Cheng-Ting Shih, Taichung (TW); Hung-Chuan Hsu, Taichung (TW); Yi-Cheng Liu, Taichung (TW)

(73) Assignees: HIWIN TECHNOLOGIES CORP., Taichung (TW); CHINA MEDICAL UNIVERSITY, Taichung (TW)

( * ) Notice: Subject to any disclaimer, the term of this patent is extended or adjusted under 35 U.S.C. 154(b) by 0 days.

(21) Appl. No.: 16/393,804

(22) Filed: Apr. 24, 2019

(65) Prior Publication Data

US 2020/0342601 A1 Oct. 29, 2020

(51) Int. Cl.
*G06T 7/00* (2017.01)
*A61B 6/03* (2006.01)
*A61B 6/00* (2006.01)

(52) U.S. Cl.
CPC ............ *G06T 7/0014* (2013.01); *A61B 6/032* (2013.01); *A61B 6/505* (2013.01); *A61B 6/5282* (2013.01);

(Continued)

(58) Field of Classification Search
CPC ......... G06T 7/0014; G06T 2207/10081; G06T 2207/30008; A61B 6/032; A61B 6/505; A61B 6/5282; A61B 6/583
See application file for complete search history.

(56) References Cited

U.S. PATENT DOCUMENTS

2006/0008046 A1* 1/2006 Ruhrnschopf ....... G01N 23/046
378/7
2010/0202001 A1* 8/2010 Miller .................... A61B 6/583
358/1.9

(Continued)

FOREIGN PATENT DOCUMENTS

TW 201825050 A 7/2018

*Primary Examiner* — Blake C Riddick
(74) *Attorney, Agent, or Firm* — Muncy, Geissler, Olds & Lowe, P.C.

(57) ABSTRACT

A method for converting scan information of computed tomography scanner into bone parameters includes the steps of: providing a computed tomography scanner; providing a test object and two phantoms of known components; using the computed tomography scanner to obtain a corresponding test object scan information and two phantoms scan information; receiving the test object scan information and the two phantoms scan information through a computing device; using the computing device to calculate an energy attenuation coefficient of the computed tomography scanner through a physical function model including the known components and the two phantoms scan information; providing the computing device with an energy correction coefficient; and enabling the computing device to obtain a bone parameter of the test object through a true relationship function that includes the energy attenuation coefficient, the test object scan information and the energy correction coefficient.

5 Claims, 2 Drawing Sheets

(52) U.S. Cl.
CPC .... *A61B 6/583* (2013.01); *G06T 2207/10081* (2013.01); *G06T 2207/30008* (2013.01)

(56) References Cited

U.S. PATENT DOCUMENTS

| | | | |
|---|---|---|---|
| 2012/0041685 A1* | 2/2012 | Ding | A61B 6/032 |
| | | | 702/19 |
| 2012/0263360 A1* | 10/2012 | Zhu | G06T 5/002 |
| | | | 382/131 |
| 2016/0166224 A1* | 6/2016 | Zhou | A61B 6/542 |
| | | | 378/16 |
| 2018/0228461 A1* | 8/2018 | Kopperdahl | A61B 6/582 |
| 2019/0239843 A1* | 8/2019 | Bregman-Amitai | |
| | | | A61B 6/5217 |
| 2019/0336097 A1* | 11/2019 | Bregman-Amitai | G06K 9/627 |
| 2020/0126271 A1* | 4/2020 | Liang | G06T 11/006 |

\* cited by examiner

METHOD FOR CONVERTING SCAN INFORMATION OF A COMPUTED TOMOGRAPHY SCANNER INTO BONE PARAMETERS

BACKGROUND OF THE INVENTION

1. Field of the Invention

The present invention relates to a method for obtaining a bone parameter of a test object and more particularly, to a method for converting scan information of a computed tomography scanner into bone parameters.

2. Description of the Related Art

Bone mineral density examinations are usually performed using special equipment such as dual-energy X-ray absorptiometry (DEXA) or quantitative computed tomography (QCT) scanners.

The dual-energy X-ray absorptiometry (DEXA) technique uses X-rays of two different energies to scan the examined tissue. X-rays that have passed through the examined tissue are received by the scintillation detector and processed by computer to obtain bone density.

The quantitative computed tomography (QCT) scanner technique is divided into two types: phantom mode and no phantom mode. With the quantitative computed tomography scanner (QCT) technique of the phantom mode, the examined tissue should be scanned synchronously with the phantom of known density. The results of the phantom scan are used as a reference, and the scan information of the examined tissue is compared with the scan information of the phantom to obtain the bone density. With the quantitative computed tomography (QCT) scanner technique of the no phantom mode, the scan information of muscle and adipose tissue is used as a reference, and the bone density is obtained by comparing with the scan information of the examined tissue. The disadvantage of QCT is that the radiation dose is large, and the scanning time is long, and the measurement accuracy is relatively lower.

As can be seen from the above, bone density is currently checked using a special equipment.

In addition, although computed tomography (CT) scanners have been widely used in biological tissue detection, currently computed tomography (CT) scanners can only construct 3D images/scans of the examined tissue and cannot distinguish the bone parameters.

SUMMARY OF THE INVENTION

The present invention has been accomplished under the circumstances in view. It is the main object of the present invention to provide a method for converting scan information of a computed tomography scanner into bone parameters of the test object by obtaining the energy attenuation coefficient of the computed tomography scanner itself, improving the bone test capability.

To achieve this and other objects of the present invention, a method for converting scan information of a computed tomography scanner into bone parameters includes the steps of: providing a computed tomography scanner; providing a test object and two phantoms of known components; using the computed tomography scanner to scan the test object and the two phantoms so as to obtain a corresponding test object scan information and phantom scan information; receiving the test object scan information and the phantom scan information through a computing device; using the computing device to calculate the energy attenuation coefficient of the computed tomography scanner through a physical function model comprising the known components of the two phantoms and the phantom scan information; providing the computing device with an energy correction coefficient that is related to an energy attenuation coefficient of the known components of the two phantoms and an energy attenuation coefficient of an ideal test object; and enabling the computing device to obtain a bone parameter of the test object through a true relationship function that comprises the energy attenuation coefficient of the computed tomography scanner, the test object scan information and the energy correction coefficient.

In this way, the present invention can obtain the energy attenuation coefficient of the computed tomography scanner through the two phantoms of the known components and the corresponding phantom scan information, and then obtain the bone parameter of the scan information of the test object through the energy attenuation coefficient and the energy correction coefficient.

Other advantages and features of the present invention will be fully understood by reference to the following specification in conjunction with the accompanying drawings, in which like reference signs denote like components of structure.

DETAILED DESCRIPTION OF THE INVENTION

Hereinafter, the technical features and achievement of the method for converting scan information of a computed tomography scanner into bone parameters of the present invention will be described with reference to the annexed drawings. However, the sequence of steps and the number of steps of the method for converting scan information of the computed tomography scanner into bone parameters are only used to illustrate the technical features of the present invention, and not to limit the present invention.

Figure 1:
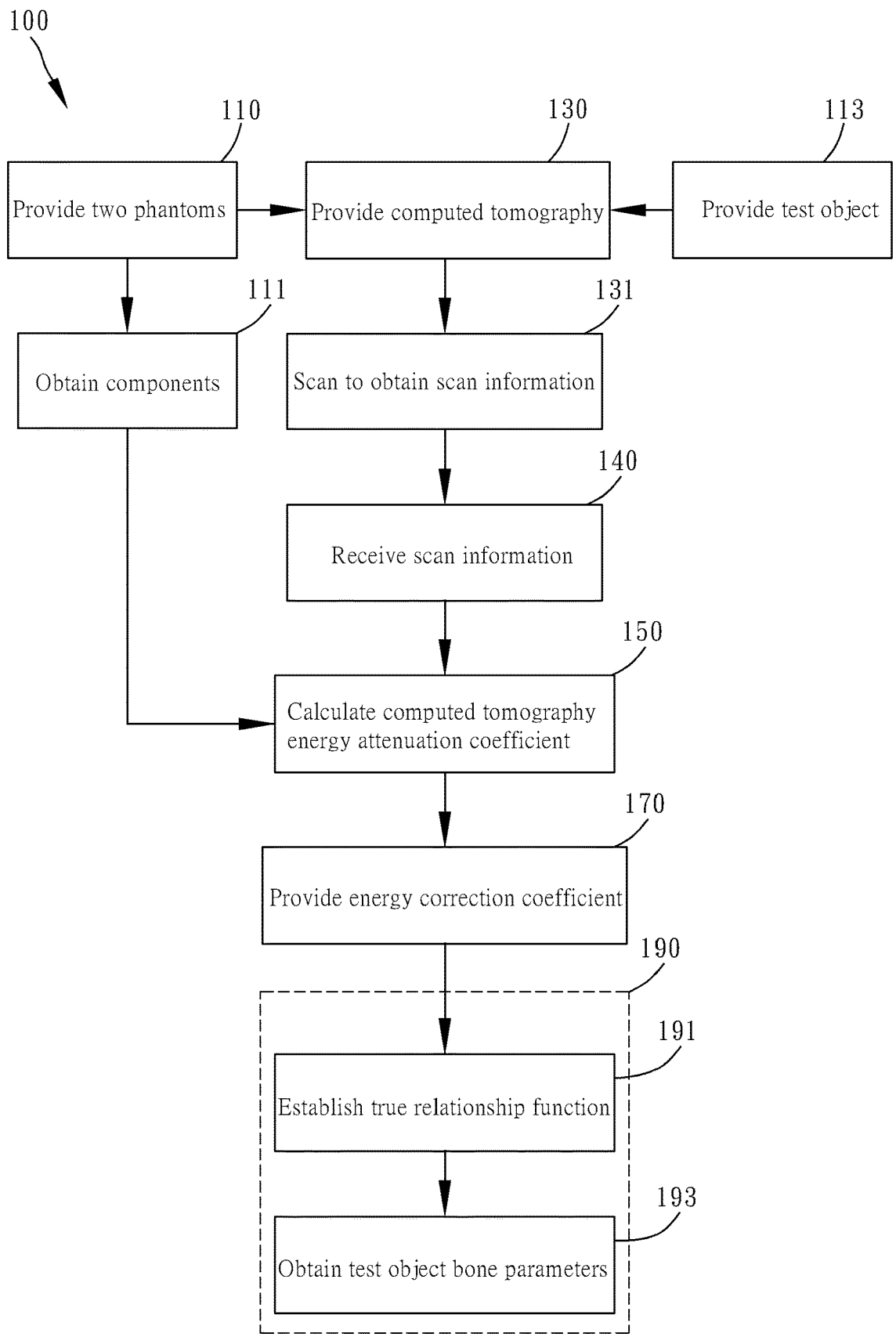
FIG. 1 is a flow chart of a method for converting scan information of a computed tomography scanner into bone parameters in accordance with the present invention.

As illustrated in FIG. 1, the method for converting scan information of a computed tomography scanner into bone parameters 100 is implemented by the steps in FIG. 1, but in other embodiments, the number of steps may be less or more, and the sequence of the steps may be adjusted, therefore, the number and sequence of the steps are not limited to the present preferred embodiment.

Step 110 is to provide two phantoms. Step 111 is to analyze two phantoms. Among them, the analysis step can obtain the components of the two phantoms and the test object through known component analysis. Step 113 is to provide a test object. In this embodiment, the test object is a biologic bone. The biologic bone comprises cortical and marrow. The parameters or ratios described in the known components of the embodiment are for illustrative purposes and are not intended to limit the present invention.

In this embodiment, the composition of the phantom is a mixture of dipotassium phosphate ($K_2HPO_4$) and water ($H_2O$). The phantom is produced by mixing a certain proportion of dipotassium phosphate and water into a cavity and forming a multi-segment skeletal phantom after dipotassium phosphate is completely dissolved. The filling solution of each segment of the phantom represents a different equivalent density of phantom, and the equivalent density of phantom ranges from 0.1 to 0.9 g/cm3. The phantom has a plurality of different partitions, and the ratio of the phantom parameters in each partition is different, and the ratio of the materials in the same partition needs to be homogeneous.

The ratio of the above two phantoms is different. Subsequently, the two phantoms are referred to as the first phantom and the second phantom, respectively, and the ratios of the first phantom and the second phantom are expressed in the following Table I. V1 and V2 respectively represent the volume percentage values, and the two are different. W1 and W2 represent values of a specific weight percentage, respectively, and the two are different. $\rho_1$, $\rho_2$ represent different densities of the first phantom and the second phantom. Therefore, phantom of different compositions and ratios can be made according to Table I.

TABLE I

Phantom composition ratio table

| | volume percentage | | weight percentage | | density |
|---|---|---|---|---|---|
| | $K_2HPO_4$ | $H_2O$ | $K_2HPO_4$ | $H_2O$ | $\rho$ (g/cm³) |
| 1st phantom | V1 | 1-V1 | W1 | 1-W1 | $\rho_1$ |
| 2nd phantom | V2 | 1-V2 | W2 | 1-W2 | $\rho_2$ |

Table II is the relevant values of the volume percentage, weight percentage, density and scan information of the components of the first phantom, the second phantom and water obtained according to Table I. The values in the table are for illustrative purposes only and are not limiting of the invention.

TABLE II

Phantom and water composition ratio table

| | volume percentage | | weight percentage | | Density | Scan information |
|---|---|---|---|---|---|---|
| | $K_2HPO_4$ | $H_2O$ | $K_2HPO_4$ | $H_2O$ | $\rho$ (g/cm3) | CT number |
| 1st phantom | 0.04098 | 0.9590 | 0.0944 | 0.9056 | 1.135936 | 181 |
| 2nd phantom | 0.08196 | 0.9180 | 0.1789 | 0.8211 | 1.257616 | 328 |
| water | 0 | 1 | 0 | 1 | 1 | 0 |

The atomic number ($Z_i$) and atomic weight ($A_i$) of each element (K, H, P, and O) of $K_2HPO_4$ and $H_2O$ can be obtained through the periodic table, as illustrated in Table III, and then the weight percentage ($W_i$) of each element of $K_2HPO_4$ and $H_2O$ and density ($\rho_m$) of $K_2HPO_4$ and $H_2O$ can be obtained through Table I.

TABLE III

Potassium phosphate ($K_2HPO_4$) composition table

| | H | O | P | K |
|---|---|---|---|---|
| Atomic number ($Z_i$) | 1 | 8 | 15 | 19 |
| Atomic weight ($A_i$) | 1.008 | 16 | 30.97 | 39.1 |

| Weight percentage ($W_i$) | | | | p (g/cm³) |

TABLE III-continued

Potassium phosphate ($K_2HPO_4$) composition table

| $K_2HPO_4$ | 0.58 | 36.74 | 17.78 | 44.9 | 2.44 |
|---|---|---|---|---|---|
| $H_2O$ | 11.19 | 88.81 | 0 | 0 | 1 |

Step 130 is to provide a computed tomography (CT) scanner. The computed tomography scanner establishes stereoradiographic medical images through digital geometric operations. The computed tomography scanner can be any device with a photon collimator, such as multi-row detector CT or dual-energy CT. In this embodiment, the single-scan mono-energy coefficient correction is adopted, so that the number of scans and the amount of radiation exposure can be reduced, but in other embodiments, the computed tomography scanner can also adopt dual-energy CT imaging.

Step 131 is to scan the first phantom, the second phantom, and the test object so as to obtain the corresponding first phantom scan information (CT number), second phantom scan information, and test object scan information. The scan information is also called the CT number (hounsfield unit, HU), and the CT number ($CTN_m$) is the unit of measurement of the local tissue of the test object, and also represents the optical attenuation value.

Step 140 is to receive the scan information of the test object, the scan information of the first phantom and the scan information of the second phantom.

Step 150 is to calculate the energy attenuation coefficient of the computed tomography scanner. The energy attenuation coefficient is based on the components of the first phantom and the second phantom, the first phantom scan information, the second phantom scan information, the physical function model corresponding to the first phantom, and the physical function model corresponding to the second phantom.

The physical function model referred to in step 150 includes equation (1) and equation (2). Equation (1) is used to calculate the optical attenuation value $\mu_m$, and $m$ of $\mu_m$ can represent any of the first phantom, the second phantom, and the water by any number or symbol. $N_A$ is the Avogadro constant; $\rho_m$ is the density; $W_i$ is the weight percentage; $A_i$ is the atomic weight; $Z_i$, $Z_{RS,i}^{a+1}$, $Z_{PE,i}^{a+1}$ are coefficients related to the atomic number; $k_1$, $k_2$ represent the energy attenuation coefficient of the computed tomography scanner. $k_1$ is the Rayleigh scattering coefficient of the energy attenuation coefficient of the computed tomography scanner and $k_2$ is the photoelectric absorption coefficient of the energy attenuation coefficient of the computed tomography scanner. The Avogadro constant is 6.022E23.

The equation (2) represents the CT number on the left side of the equal sign and the optical attenuation value $\mu_m$ of the phantom (test object) divided by the optical attenuation value $\mu_{H_2O}$ of the water on the right side of the equal sign.

The CT number represented by the equation (2) on the left side of the equal sign is the CT number ($CTN_m$) of each phantom captured by the computed tomography scanner.

The CT number is converted by the equation (2) to become the equivalent value of the optical attenuation value $\mu_m$ of the phantom (test object) divided by the optical attenuation value $\mu_{H_2O}$ of the water.

$$\mu_m = \rho_m N_A \sum_{i=1}^{N} \left( \frac{W_i}{A_i} (Z_i + Z_{RS,i}^{d+1} \cdot k_1 + Z_{PE,i}^{a+1} \cdot k_2) \right) \quad \text{equation (1)}$$

$$\frac{CTN_m}{1000} + 1 = \frac{\mu_m}{\mu_{H_2O}} \quad \text{equation (2)}$$

In equation (1), $Z_i$ is the atomic number of the $i^{th}$ element. For example, H (hydrogen) is 1, oxygen (O) is 8. $Z_{RS,i}^{d+1}$ is an effective atomic number for Rayleigh scattering, $Z_{PE,i}^{a+1}$ is an effective atomic number for photoelectric absorption, as described in Attix, F. H. (2008). Introduction to radiological physics and radiation dosimetry. John Wiley & Sons. In addition, d in the effective atomic number of the photoelectric absorption and a of the effective atomic number of the Rayleigh scattering can be referred to Rutherford, R. A., Pullan, B. R., & Isherwood, I. (1976). Measurement of effective atomic number and electron density using an EMI scanner. Neuroradiology, 11(1), 15-21, Rutherford. In this embodiment, d is 1.86, a is 3.62. Take oxygen as an example, $Z_{RS,i}^{d+1}$ is 14868.79384, $Z_{PE,i}^{a+1}$ is 382.6814077. The relevant parameters are as shown in Table IV. These parameters are for illustrative purposes only and are not intended to limit the invention.

TABLE IV

| | $\sum_{i=1}^{N}\left(\frac{W_i}{A_i}(Z_i)\right)$ | $\sum_{i=1}^{N}\left(\frac{W_i}{A_i}(Z_{RS,i}^{d+1})\right)$ | $\sum_{i=1}^{N}\left(\frac{W_i}{A_i}(Z_{PE,i}^{a+1})\right)$ | $\rho$ (g/cm3) |
|---|---|---|---|---|
| $1^{st}$ phantom | 8.7164 | 49558.288 | 296.513 | 1.135936 |
| $2^{nd}$ phantom | 9.6455 | 85106.255 | 377.137 | 1.257616 |
| water | 7.3063 | 16310.604 | 216.610 | 1 |

Substitute the values of the parameters in Table IV into equation (1) to calculate the optical attenuation value $\mu_1$ of the first phantom, the optical attenuation value $\mu_2$ of the second phantom, and the optical attenuation value $\mu_{H_2O}$ of the water.

In equation (1), $\rho_m$, $N_A$, $Z_{RS,i}^{d+1}$, atomic number ($Z_i$), atomic weight ($A_i$) and weight percentage ($W_i$) can be obtained from the corresponding constant values of physical components. Therefore, the only unknown parameters in equation (1) are the energy attenuation coefficients $k_1$ and $k_2$.

Then, the optical attenuation value $\mu_1$ of the first phantom, the optical attenuation value $\mu_2$ of the second phantom, and the optical attenuation value $\mu_{H_2O}$ of the water obtained by the equation (1) in step 150 are substituted into the equation (2). The CT numbers of the first phantom and the second phantom in Table II are then used to construct two proportional equations based on the optical attenuation value $\mu_1$ of the first phantom and the optical attenuation value $\mu_2$ of the second phantom relative to the optical attenuation value $\mu_{H_2O}$ of the water. Therefore, solving the two proportional equations can obtain the energy attenuation coefficients $k_1$ and $k_2$ of the computed tomography scanner. In this embodiment, the energy attenuation coefficients $k_1$ and $k_2$ are −4.960584907 and 0.010816298 respectively.

Therefore, the description of Step 150 shows that the number of phantom needs only at least two, but the number of phantom can be more, not limited to two.

Next, Step 170 is to provide an energy correction coefficient X. The energy correction coefficient X is corrected by the energy dependence of the specific components of the ideal bone and the phantom.

For the energy attenuation coefficient of an ideal bone, you can search the XCOM:Photon Cross-Section Database of the National Institute of Standards and Technology (NIST) and Tissue Substitutes in Radiation Dosimetry and Measurement Report-44 of International Commission on Radiation Units and Measurements (ICRU) to query internationally permissible recommendations for physical quantities, radiated units and radioactivity, as well as integrated metrics and physical data. The energy correction coefficient is the ratio of the energy attenuation coefficient of the principal component of the phantom (dipotassium phosphate) divided by the energy attenuation coefficient of the ideal bone.

Step 190 includes sub step 191 to establish a true relationship function, and sub step 193 to obtain the bone parameter of the test object. In other words, step 190 is to obtain the bone parameter of the test object through the true relationship function. The true relationship function is as shown in equation (3) to obtain the correspondence between the optical attenuation value $\mu_B$ of the test object and the CT number ($CTN_B$) taken by the computed tomography scanner. Equation (3) is related to the energy attenuation coefficients $k_1$ and $k_2$ of the computed tomography scanner, the test object scan information ($CTN_B$) and the energy correction coefficient X. The difference between equation (3) and equation (2) is that equation (3) is corrected by the energy correction coefficient to improve the accuracy of obtaining the optical attenuation value $\mu_B$ of the test object. Thus, the optical attenuation value $\mu_B$ can be put into equation (1) to obtain bone parameters such as bone density $\rho_B$.

$$\frac{CTN_B}{1000} + 1 = \frac{\mu_B}{\mu_{H_2O}} * X \quad \text{equation (3)}$$

Thus, because commercial (commercially available) computed tomography scanner has different energy attenuation coefficients, and non-fixed constants. Therefore, the energy attenuation coefficients $k_1$ and $k_2$ of the computed tomography scanner can be obtained through step 150. Therefore, commercial computed tomography scanner can obtain the relevant energy attenuation coefficient through this step. Then, the energy correction coefficient is obtained through step 170 to make the true relationship function established in step 190 more accurate.

The present invention can obtain the density parameter of the biological bone through the above steps and the CT number of the computed tomography scanner, thereby contributing to the surgical planning and improving the quality. For example, when performing an orthopedic operation, the medical staff can understand the density parameters of the bone segments from the bone density parameter and can easily select the fixing position with better bone density to fix the bone nail/screw.

The calculation of step 150 is performed by a built-in computing device of the computed tomography scanner or an external computing device. In other words, equation (1) and equation (2) can be established in the computing device for processing and computing by the computing device whether it is a built-in computing device or an external computing device.

Step 170 is achieved by providing an energy correction coefficient X to the computing device via an input or a preset program. The step 190 of establishing true relationship function is to establish the true relationship function in a computing device built in the computed tomography scanner or an external computing device. Thus, when the CT number (scan information) of the target bone is detected by the computed tomography scanner corresponding to the energy attenuation coefficients $k_1$ and $k_2$ of the computed tomography scanner, the bone density parameter of the target bone can be obtained through the corresponding true relationship function.

The computing device converts the CT numbers scanned by the computed tomography scanner into medical images or scan information containing test object bone parameters (e.g, density).

Figure 2:
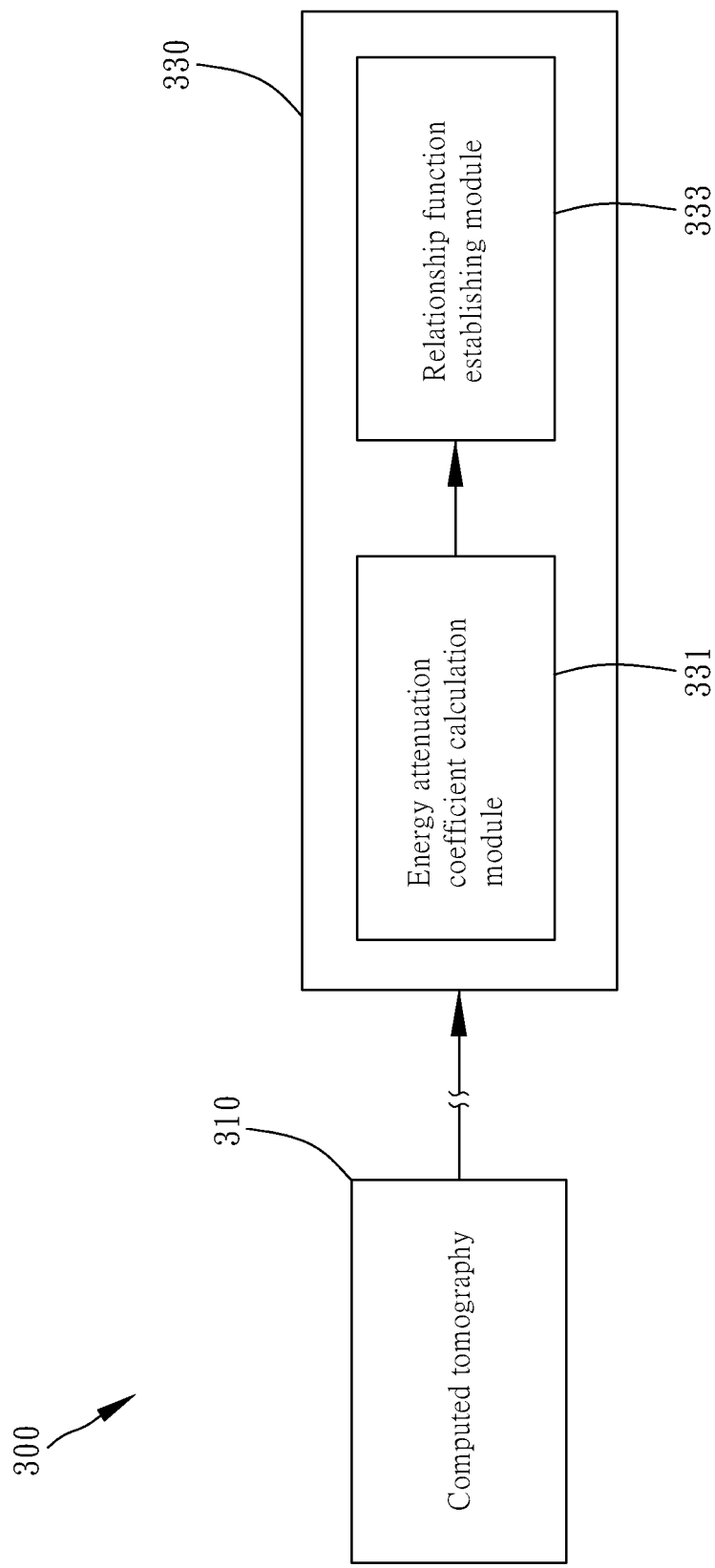
FIG. 2 is a schematic diagram of the conversion system performing FIG. 1.

As shown in FIG. 2, the conversion system 300 comprises a computed tomography scanner 310 and a computing device 330. The computing device 330 comprises an energy attenuation coefficient calculation module 331 and a relationship function establishing module 333. The relationship function establishing module 333 is electrically connected to the energy attenuation coefficient calculation module 331.

The computed tomography scanner 310 is coupled to the computing device 330. The coupling may be a wired connection, a wireless connection, or a storage medium to provide scan information to the computing device 330 for the computing device to perform step 140. Further, the computed tomography scanner 310 may be more than one, for example, two, three, or more many.

The energy attenuation coefficient calculation module 331 performs step 150. The energy attenuation coefficient calculation module 331 can receive the scan information (step 131) and execute the physical function model according to the scan information (step 150) to obtain the energy attenuation coefficients $k_1$ and $k_2$ corresponding to the computed tomography scanner.

The relationship function establishing module 333 performs step 170 and step 190. The energy correction coefficient X in step 170 is stored or established in the relationship function establishing module 333. The true relationship function in step 190 is also established in the relationship function establishing module 333.

In this way, the computing device and the conversion method thereof of the present invention can obtain the energy attenuation coefficient of the computed tomography scanner through the scan information captured by the computed tomography scanner and the known phantom component conversion. The energy attenuation coefficient is used to obtain the bone parameters of the test object. The bone parameters include density and distribution. Thus, the state of the bone can be obtained more accurately during the operation planning to improve efficiency and medical quality.

In other embodiments, the energy attenuation coefficient calculation module 331 and the relationship function establishing module 333 can be performed through different computing devices, i.e., the energy attenuation coefficient calculation module is established in one computing device and the relationship function establishing module is established in the other computing device. For example, one computing device is used to perform step 150, the other computing device is used to receive the energy attenuation coefficient of the computed tomography scanner. Through the above-described step 170 and step 190, the bone parameter of the test object is obtained. Therefore, the computing device is not limited to a single one.

Finally, it is emphasized that the order of the steps and the constituent elements disclosed in the foregoing embodiments are merely illustrative and are not intended to limit the scope of the present invention. Changes in the order of steps, substitutions or changes in equivalent components should also be covered by the scope of the present invention.

What is claimed is:

1. A method for converting scan information of a computed tomography scanner into bone parameters, comprising the steps of:
   providing a computed tomography scanner;
   providing a test object and two phantoms of known components;
   using the computed tomography scanner to scan the test object and the two phantoms to obtain respectively test object scan information and phantom scan information;
   receiving the test object scan information and the phantom scan information through a computer;
   using the computer to calculate an energy attenuation coefficient of the computed tomography scanner using a physical function model corresponding to the two phantoms, the physical function model comprising the known components of two phantoms and the phantom scan information;
   providing an energy correction coefficient to the computer, the energy correction coefficient being related to an energy attenuation coefficient of the known components of the two phantoms and an energy attenuation coefficient of an ideal test object; and
   enabling the computer to obtain a bone parameter of the test object using a true relationship function, the true relationship function comprising the energy attenuation coefficient of the computed tomography scanner, the test object scan information, and the energy correction coefficient.

2. The method for converting scan information of a computed tomography scanner into bone parameters as claimed in claim 1, wherein the known components of the two phantoms comprises a density, a weight percentage, anatomic weight and an atomic number of elements of dipotassium phosphate and water.

3. The method for converting scan information of a computed tomography scanner into bone parameters as claimed in claim 1, wherein the energy attenuation coefficient comprises a photoelectric absorption coefficient and a Rayleigh scattering coefficient.

4. The method for converting scan information of a computed tomography scanner into bone parameters as claimed in claim 1, wherein the physical function model comprises:

$$\mu_m = \rho_m N_A \sum_{i=1}^{N} \left( \frac{W_i}{A_i} (Z_i + Z_{RS,i}^{d+1} \cdot k_1 + Z_{PE,i}^{a+1} \cdot k_2) \right)$$

$$\frac{CTN_m}{1000} + 1 = \frac{\mu_m}{\mu_{H_2O}}$$

in which, $\mu_m$ is an optical attenuation value of the two phantoms; $\mu_{H_2O}$ is an optical attenuation value of the water; $N_A$ is the Avogadro constant; $\rho_m$ is a density; $W_i$ is a weight percentage of a $i^{th}$ element; $A_i$ is the atomic weight of the $i^{th}$ element; $Z_i$ is the atomic number of the $i^{th}$ element; $Z_{RS,i}^{d+1}$ is an effective atomic number for Rayleigh scattering; $Z_{PE,i}^{a+1}$ is an effective atomic number for photoelectric absorption; $k_1$ is a Rayleigh scattering coefficient of the computed tomography scanner; $k_2$ is a photoelectric absorption coefficient of the computed tomography scanner; $CTN_m$ is the scan information of the computed tomography scanner.

5. The method for converting scan information of a computed tomography scanner into bone parameters as claimed in claim 1, wherein the true relationship function comprises:

$$\frac{CTN_B}{1000} + 1 = \frac{\mu_B}{\mu_{H_2O}} * X$$

wherein $CTN_B$ is the scan information of the test object, $\mu_B$ is an optical attenuation value of the test object, X is the energy correction coefficient.

* * * * *